(12) United States Patent
Boyd

(10) Patent No.: US 7,654,267 B2
(45) Date of Patent: Feb. 2, 2010

(54) INTRAORAL DISCLUDER AND METHOD FOR RELIEVING MIGRAINE AND TENSION HEADACHES AND TEMPOROMANDIBULAR DISORDERS

(75) Inventor: James P. Boyd, Rancho Sante Fe, CA (US)

(73) Assignee: NTI-TSS, Inc., Rancho Sante Fe, CA (US)

( * ) Notice: Subject to any disclaimer, the term of this patent is extended or adjusted under 35 U.S.C. 154(b) by 624 days.

(21) Appl. No.: 10/881,946

(22) Filed: Jun. 29, 2004

(65) Prior Publication Data
US 2005/0288624 A1    Dec. 29, 2005

(51) Int. Cl.
*A61C 3/00*  (2006.01)
*A61C 5/14*  (2006.01)

(52) U.S. Cl. .................... 128/859; 128/861; 433/6
(58) Field of Classification Search ......... 128/859–862, 128/846, 848; 433/6, 41; 602/902
See application file for complete search history.

(56) References Cited

U.S. PATENT DOCUMENTS

| | | | | |
|---|---|---|---|---|
| 3,510,946 | A * | 5/1970 | Kesling | 433/6 |
| 5,085,584 | A | 2/1992 | Boyd | 433/6 |
| 5,427,117 | A | 6/1995 | Thornton | 128/848 |
| 5,513,656 | A | 5/1996 | Boyd, Sr. | 128/859 |
| 5,678,567 | A | 10/1997 | Thornton et al. | 128/848 |
| 5,682,903 | A * | 11/1997 | Meade | 128/848 |
| 5,779,470 | A * | 7/1998 | Kussick | 433/6 |
| 5,795,150 | A | 8/1998 | Boyd | 433/6 |
| 6,092,523 | A * | 7/2000 | Belfer | 128/848 |
| 6,231,337 | B1 | 5/2001 | Boyd | 433/6 |
| 6,666,212 | B2 | 12/2003 | Boyd, Sr. | 128/859 |

FOREIGN PATENT DOCUMENTS

WO    WO 03051280 A2 *  6/2003

* cited by examiner

*Primary Examiner*—Matthew F DeSanto
(74) *Attorney, Agent, or Firm*—Sheppard, Mullin, Richter & Hampton LLP

(57) ABSTRACT

An intraoral discluder for preventing chronic tension headaches, common migraine headaches, and temporomandibular disorders that are caused or perpetuated by chronic activity of the temporalis muscle. The discluder includes a trough, contoured to encompass at least one maxillary or mandibular incisor, from which extends a protruding platform, for engagement by the opposing incisors. The trough can be retained on the teeth by any adaptable material than can flow around the teeth and then maintain its shape. Once in place in the wearer's mouth, one or two opposing incisors will come into contact with the platform prior to the upper and lower posterior and/or canine teeth coming into contact, regardless of the position of the mandible, thereby reducing the intensity of the activity of the temporalis muscle. In addition, a special post on the discluder's platform is engageable directly with one or more opposing incisors, to act as a stop and thereby inhibit excessive retrusive movement of the mandible and urge the mandible toward a more protrusive position. This can reduce the intensity of undesired clenching, and it can enhance the size of the wearer's pharyngeal airspace, thereby reducing the incidence and severity of snoring.

17 Claims, 2 Drawing Sheets

INTRAORAL DISCLUDER AND METHOD FOR RELIEVING MIGRAINE AND TENSION HEADACHES AND TEMPOROMANDIBULAR DISORDERS

BACKGROUND OF THE INVENTION

The present invention relates generally to intraoral devices and, more particularly, to an intraoral discluder for use in relieving tension headaches, common migraine headaches, and temporomandibular disorders.

Tension and muscle contraction headaches affect many people every day. The headaches are often recurring and, without effective treatment, can become very painful, restricting an individual's ability to think clearly and function effectively. The discomfort associated with tension and muscle contraction headaches is usually due to pain from strained and fatigued muscles of the head. The majority of the muscles of the human head are not sufficiently strong to elicit the type of pain and discomfort associated with tension and muscle contraction headaches. That is not the case with the temporalis muscle, however, which is located on the side of the skull and extends from just behind the eye to just behind the ear, and which is an extremely powerful muscle that functions to close or elevate the jaw.

Under normal circumstances, the temporalis muscle should not exert a large static force by contracting isometrically, except possibly during normal chewing. Inappropriate isometric contraction of the temporalis muscle is commonly known as "clenching" and is clinically known as myofascial dysfunction. The intensity of the myofascial dysfunction varies according to the mandible's anterior/posterior position, with the intensity increasing as the mandible's position moves posteriorly. Unfortunately, myofascial dysfunction is particularly difficult to detect or diagnose, because the act of clenching is a relatively motionless act that is commonly done while a person is concentrating on another topic, or while sleeping.

As the muscular contraction condition of "clenching" continues, the muscle becomes fatigued and susceptible to spasm and cramping. The pain from spasming and cramping temporalis fibers is severe and is usually diagnosed as a common migraine. Headache sufferers who seek the assistance of a physician typically are treated with muscle relaxants, analgesics, and/or physical therapy for the muscle fatigue. However, medications and physical therapy require continual treatment, and they treat only the symptoms of the underlying problem, not the source of the problem itself.

Headache sufferers who seek the assistance of a dentist typically are diagnosed as having a temporomandibular disorder and are treated with an intraoral "jaw-positioning" appliance. Unfortunately, the intraoral appliances provided by dentists frequently are not entirely effective, because they only approximate the relative positions of the upper and lower teeth with respect to each other, allowing clenching to continue with minimal mandibular movement. Further, these intraoral appliances ordinarily cannot be used by patients who have malocclusions, protrusions or retrusions of the mandible, or other irregular teeth or mandibular orientations. Typically, the intraoral appliance must also be fabricated by a dentist at a prohibitive cost to a majority of individuals who suffer from tension headaches and common migraine headaches. Lastly, most intraoral jaw-positioning appliances and other types of semi-custom intraoral discluders can be used only on the upper teeth. However, in some circumstances, use of the appliance on the upper teeth is impossible due to malocclusions and irregular orientation of the teeth.

One intraoral appliance that avoids the drawbacks mentioned immediately above is disclosed in U.S. Pat. No. 5,795,150 to Boyd, Sr. That appliance includes a trough sized and configured to be releasably retained by a wearer's maxillary incisors and further includes a dome projecting posteriorly from the trough and defining a surface to be contacted by at least one opposing incisor. When the appliance is properly positioned in the wearer's mouth, the temporalis muscles are rendered ineffective, thus relieving tension headaches, common migraine headaches, and temporomandibular disorders. However, it is believed that this appliance can sometimes still allow limited clenching of the temporalis muscle, particularly when the mandible is located in its furthest posterior position.

It should be apparent from the foregoing discussion, that there remains a need for an even more effective intraoral discluder configured to be placed on either the upper teeth or the lower teeth, to prevent contact of the upper and lower teeth in all mandibular movements and to further inhibit undesired isometric contraction of the temporalis muscle. The present invention satisfies this need.

SUMMARY OF THE INVENTION

The present invention is embodied in an intraoral discluder, and related method for using it, configured not only to prevent contact of the upper and lower teeth in all mandibular movements, but also to inhibit excessive retrusive movement of the mandible, thereby reducing the intensity of undesired clenching and enhancing the size of the wearer's pharyngeal airspace. More particularly, the discluder includes a prefabricated trough having a anterior wall and a posterior wall sized and configured to accommodate at least one upper or lower incisor, and it further includes a platform attached to the trough and defining a contact surface that is spaced sufficiently from the trough to prevent contact between opposing upper and lower teeth, whether the mandible is in a protrusive position or a retrusive position. In addition, a post located at the posterior end of the platform is sized and configured to be engageable directly with one or more opposing incisors and thereby inhibit excessive retrusive movement of the mandible.

In other, more detailed features of the invention, the post is configured to inhibit excessive retrusive movement of the mandible sufficient to substantially enhance the pharyngeal airspace. Preferably, the post is configured like a planar blade, projecting away from the contact surface with an anterior surface of the post defining an acute angle with the contact surface.

The trough, platform, and post of the discluder preferably are formed integral with each other. The platform projects substantial distances both anteriorly from the trough's anterior wall and posteriorly from the trough's posterior wall, when the trough is positioned in the wearer's mouth. Further, the platform's contact surface is substantially uniform along an anterior/posterior axis, and it has a dimension that is substantially uniform in directions perpendicular to the anterior/posterior axis.

Other features, and advantages of the present invention should become apparent from the following description of the preferred embodiment, taken in conjunction with the accompanying drawings, which illustrate, by way of example, the principles of the invention.

DETAILED DESCRIPTION OF THE PREFERRED EMBODIMENT

Figure 1:
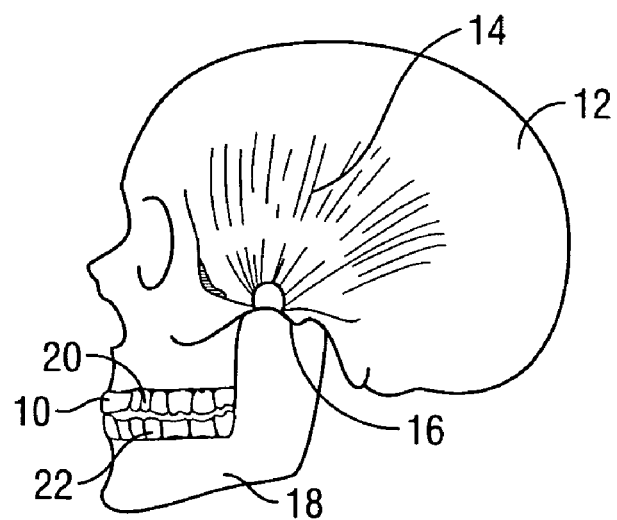
FIG. 1 is a schematic side elevation view of the human skull with a preferred embodiment of an intraoral discluder of the invention positioned over the maxillary incisors.
Figure 2:
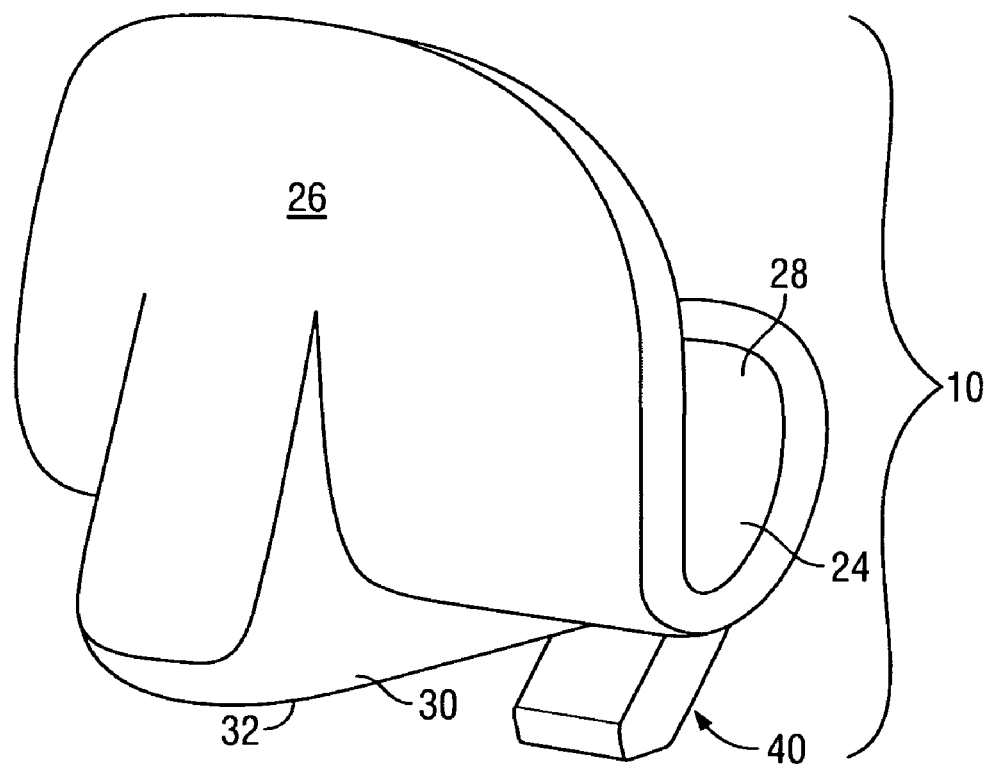
FIG. 2 is a perspective view of the intraoral discluder of FIG. 1.

With reference now to the exemplary drawings, and particularly to FIGS. 1 and 2, there is shown an intraoral discluder 10 in accordance with the invention. The discluder functions to prevent tension headaches, common migraine headaches, and temporomandibular disorders. With particular reference to FIG. 1, a schematic representation of a human skull 12 is shown, wherein the temporalis muscle 14 extends from the skull to its attachment 16 on the mandible 18. A contraction of the temporalis muscle causes the jaw to close. The discluder prevents the upper teeth 20 and the lower teeth 22 from contacting each other and thereby inhibits undesired contraction of the temporalis muscle.

As shown in FIG. 2, the intraoral discluder 10 includes a trough 24 having an anterior wall 26 and a posterior wall 28. The trough has a slight arc shape, to match the typical curve of a wearer's upper or lower incisors. A protruding rail or platform 30 projects away from the trough, to define an elongated contact surface 32 extending in a direction generally perpendicular to the axis of the trough. The trough and the protruding platform can be integral with each other or, alternatively, can be separately formed and then attached to each other. In addition, the trough and the protruding platform both can be made of any suitable biocompatible material that will hold its form, e.g., polymers, enamels, rubbers, silicone resins, and any other conventional materials known to be used by those skilled in the art. Alternatively, the trough and the protruding platform can be made of different biocompatible materials selected from these same examples.

Figure 3:
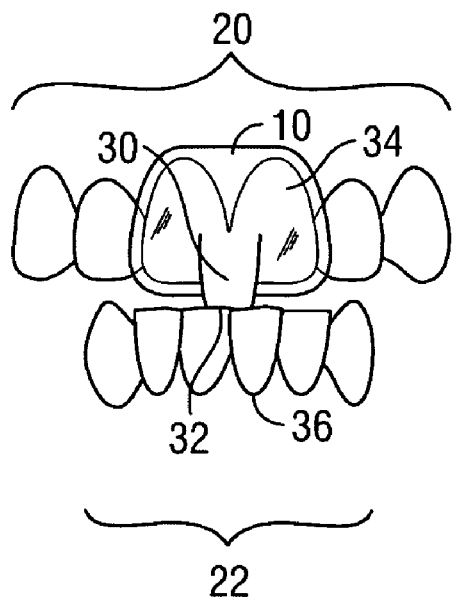
FIG. 3 is a front elevational view of the intraoral discluder of FIG. 2, in place over the maxillary incisors, opposing the mandibular incisors.

FIG. 3 shows the intraoral discluder 10 in place over the maxillary incisors 34, with the contact surface 32 of the protruding platform 30 being contacted by the opposing mandibular incisors 36 when the mandible 18 (FIG. 1) elevates. The contact surface is positioned a sufficient distance from the trough 24 to prevent the opposing upper teeth 20 and lower teeth 22 from contacting each other. Typically, this distance is on the order of several millimeters.

Figure 4:
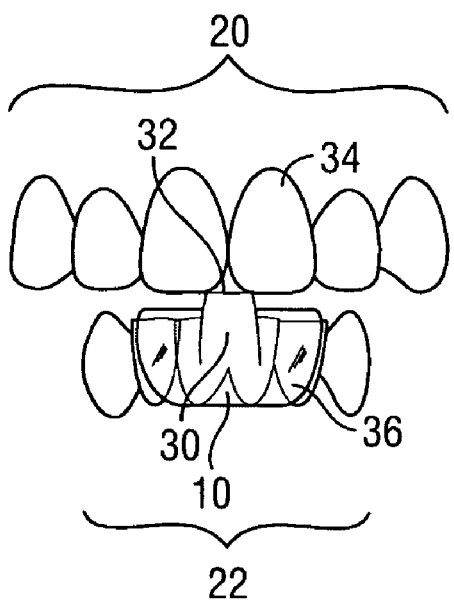
FIG. 4 is a front elevational view of the intraoral discluder of FIG. 2, in place over the mandibular incisors, opposing the maxillary incisors.

Alternatively, as shown in FIG. 4, the intraoral discluder 10 can be placed over the mandibular incisors 36, with the contact surface 32 of the protruding platform 30 contacting the opposing maxillary incisors 34 when the mandible 18 elevates. As in the case when the discluder is placed over the maxillary incisors, this prevents the opposing upper teeth 20 and lower teeth 22 from contacting each other.

Figure 5:
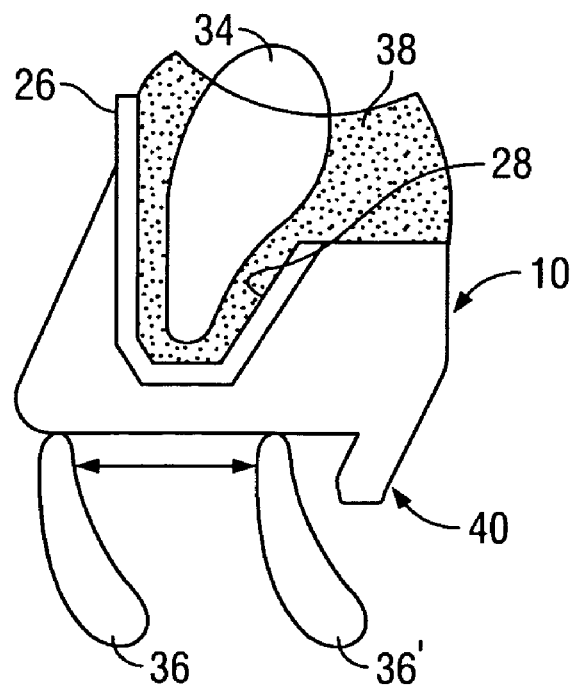
FIG. 5 is a side sectional view of the intraoral discluder of FIG. 2, in place over a maxillary incisor with an adaptable material conforming to the shape of the maxillary incisor, opposing a mandibular incisor, with the mandibular incisor shown in both a protrusive and a retrusive position.

With reference now to FIG. 5, an adaptive material 38 can optionally be disposed within the trough 24, between the anterior wall 26 and the posterior wall 28, for conforming engagement with the maxillary incisors 34. This adaptive material can be made of any type of material that conforms and retains its shape, including, e.g., silicone resins, polymers, enamels, rubbers, and any other material known to be used by those skilled in the art. This material aids in providing a comfortable and durable engagement between the discluder 10 and the incisors.

The protruding platform 30 is depicted to project both anteriorly and posteriorly from the trough 24. This ensures that the opposing mandibular incisors 36 will contact the platform's contact surface 32 regardless of whether the mandible 18 is in a protrusive position or a retrusive position. These two positions are depicted in FIG. 5, with the mandibular incisor being identified by the reference numeral 36 when in a protrusive position and by the reference numeral 36' when in a retrusive position. Preferably, the contact surface has a length in the anterior/posterior direction in the range of about 8 mm to about 12 mm and a uniform transverse width of about 5 mm. The contact surface projects anteriorly from the anterior wall 26 of the trough by at least about 3 mm.

With continued reference to FIG. 5, it will be noted that a blade-like post 40 projects away from the posterior end of the protruding platform 30. This post acts as a stop for the wearer's mandibular incisors 36, inhibiting excessive retrusive movement of the mandible 18 and urging the mandible toward a more protrusive position. This can serve two important functions. First, it can reduce the intensity of undesired clenching, and, second, it can enhance the size of the wearer's pharyngeal airspace, thereby reducing the incidence and severity of snoring.

In an alternative embodiment, not depicted in the drawings, the intraoral discluder can include one or more extending tabs sized and configured for placement onto the protruding platform, thereby increasing the distance of the contacting surface from the trough. These tabs are selectively used if the wearer's mouth is configured such that the upper and lower teeth would otherwise contact each other before the opposing incisors would contact the platform. The extension tabs can be made of any suitable biocompatible material, including, e.g., silicone resins, polymers, enamels, rubbers, and any other material known to those skilled in the art. The extension tabs may be adhered to the entire platform, as shown, or to only a portion of it, and they can be adhered by any suitable means, e.g., adhesives, cutouts, prefabricated snap-in-place pieces, natural attraction, adhesion, or other any other suitable method known to those skilled in the art.

In another alternative embodiment, not depicted in the drawings, the intraoral discluder can be configured to include one or more cutouts in the trough's anterior wall, for enhancing the retention of the adaptive material within the trough. Other structures for enhancing retention of the adaptive material can include mechanical undercuts, adhesives, and/or natural attraction of the adaptable material to the trough.

It should be evident from the drawings and the discussion above that the intraoral discluder of the invention is effective in preventing the upper teeth and lower teeth from contacting each other. This, in turn, prevents undesired isometric contractions of the temporalis muscle, thereby minimizing the occurrence of tension headaches, common migraine headaches, and temporomandibular disorders. In addition, a special post on the discluder is sized and configured to be engageable directly with one or more opposing incisors, to act as a stop and thereby inhibit excessive retrusive movement of the mandible and urge the mandible toward a more protrusive position. This can reduce the intensity of undesired clenching, and it can enhance the size of the wearer's pharyngeal airspace, thereby reducing the incidence and severity of snoring.

Although the invention has been described in detail with reference to the presently preferred embodiments, those of ordinary skill in the art will appreciate that various modifications can be made without departing from the invention. Accordingly, the invention is defined only by the following claims.

I claim:

1. An intraoral discluder comprising:
   a trough assembly including an adaptive material having an anterior wall and a posterior wall sized and configured to conformably engage at least one upper or lower incisor, wherein the anterior wall is disposed adjacent to the incisor's labial side and the posterior wall is disposed adjacent to the incisor's lingual side when the trough assembly is disposed in the wearer's mouth;
   a platform attached to the trough assembly and defining a contact surface for direct contact with opposing incisors along the entire contact surface, wherein the contact surface projects a substantial distance posteriorly from the trough assembly's posterior wall when the trough assembly is disposed in the wearer's mouth, wherein the contact surface is spaced sufficiently from the trough assembly to prevent contact between opposing upper and lower teeth, whether the mandible is in a protrusive position or a retrusive position, and wherein the platform's contact surface is substantially uniform along an anterior/posterior axis when the discluder is positioned in the wearer's mouth; and
   a post located at the posterior end of the platform and projecting in a direction away from the trough assembly, wherein the post is sized and configured to be engageable directly with one or more opposing incisors, to inhibit excessive retrusive movement of the mandible.

2. An intraoral discluder as defined in claim 1, wherein the post is configured like a planar blade, projecting away from the contact surface.

3. An intraoral discluder as defined in claim 2, wherein the post's contact surface has a dimension that is substantially uniform in directions perpendicular to the anterior/posterior axis.

4. An intraoral discluder as defined in claim 1, wherein the post is configured to inhibit excessive retrusive movement of the mandible sufficient to substantially enhance the pharyngeal airspace.

5. An intraoral discluder as defined in claim 1, wherein the trough assembly, the platform, and the post are integral with each other.

6. An intraoral discluder as defined in claim 1, wherein the platform also projects a substantial distance anteriorly from the trough assembly's anterior wall, when the trough assembly is positioned in the wearer's mouth.

7. An intraoral discluder as defined in claim 1, wherein the post has an anterior surface that defines an acute angle with the platform's contact surface.

8. An intraoral discluder as defined in claim 1, wherein the trough assembly is sized and configured to accommodate only the upper or lower incisors.

9. An intraoral discluder comprising:
   a trough having an anterior wall and a posterior wall sized and configured to accommodate at least one upper or lower incisor, wherein the anterior wall is disposed adjacent to the incisor's labial side and the posterior wall is disposed adjacent to the incisor's lingual side when the trough is disposed in the wearer's mouth;
   a platform integral with the trough and defining an elongated, substantially uniform contact surface extending generally along an anterior/posterior axis when the discluder in positioned in the wearer's mouth, wherein the contact surface projects a substantial distance anteriorly of the trough's anterior wall and a substantial distance posteriorly of the trough's posterior wall, and wherein the contact surface is spaced sufficiently from the trough to prevent contact between opposing upper and lower teeth, whether the mandible is in a protrusive position or a retrusive position; and
   a blade-like post located at the posterior end of the platform and projecting in a direction away from the contact surface, wherein the post has an anterior surface that defines an acute angle with the contact surface, and wherein the post is sized and configured to be engageable directly with one or more opposing incisors, to inhibit excessive retrusive movement of the mandible thereby substantially enhance the pharyngeal airspace.

10. A method for preventing undesired contraction of the temporalis muscle, comprising the steps of:
    providing an intraoral discluder that includes,
      a trough assembly including an adaptive material having an anterior wall and a posterior wall sized and configured to conformably engage at least one upper or lower incisor, wherein the anterior wall is disposed adjacent to the incisor's labial side and the posterior wall is disposed adjacent to the incisor's lingual side when the trough assembly is disposed in the wearer's mouth,
      a protruding platform attached to the trough assembly and having a contact surface for direct contact with opposing incisors along the entire contact surface, wherein the contact surface extends a substantial distance posteriorly from the posterior wall of the trough assembly when the trough assembly is disposed in the wearer's mouth, wherein the platform's contact surface is substantially uniform along an anterior/posterior axis when the discluder is positioned in the wearer's mouth, and wherein the contact surface is spaced sufficiently from the trough to prevent contact between opposing upper and lower teeth, whether the mandible is in a protrusive position or a retrusive position, and
      a post disposed at the posterior end of the protruding platform's contact surface and configured to project away from the contact surface; and
    placing the intraoral discluder on at least one of the wearer's upper or lower incisors so that at least one opposing incisor will contact the protruding platform and thereby prevent direct contact between wearer's upper and lower teeth, whether the mandible is in a protrusive position or a retrusive position;
    wherein the post is sized and configured to be engageable directly with one or more opposing incisors, to inhibit excessive retrusive movement of the mandible.

11. An intraoral discluder comprising:
    a trough having an anterior wall and a posterior wall sized and configured to accommodate at least one upper or lower incisor, wherein the anterior wall is disposed adjacent to the incisor's labial side and the posterior wall is disposed adjacent to the incisor's lingual side when the trough is disposed in the wearer's mouth;
    a platform attached to the trough and defining a contact surface that projects a substantial distance posteriorly from the trough's posterior wall when the trough is disposed in the wearer's mouth, wherein the contact surface is spaced sufficiently from the trough to prevent contact between opposing upper and lower teeth, whether the mandible is in a protrusive position or a retrusive position; and
    a post located at the posterior end of the platform and projecting in a direction away from the trough, wherein the post has an anterior surface that defines an acute angle with the platform's contact surface, and wherein the post is sized and configured to be engageable directly with one or more opposing incisors, to inhibit excessive retrusive movement of the mandible.

12. An intraoral discluder as defined in claim 11, wherein the platform's contact surface is substantially uniform along an anterior/posterior axis, when the discluder is positioned in the wearer's mouth, and the post is configured like a planar blade, projecting away from the contact surface.

13. An intraoral discluder as defined in claim 12, wherein the post's contact surface has a dimension that is substantially uniform in directions perpendicular to the anterior/posterior axis.

14. An intraoral discluder as defined in claim 11, wherein the post is configured to inhibit excessive retrusive movement of the mandible sufficient to substantially enhance the pharyngeal airspace.

15. An intraoral discluder as defined in claim 11, wherein the trough, the platform, and the post are integral with each other.

16. An intraoral discluder as defined in claim 11, wherein the platform also projects a substantial distance anteriorly from the trough's anterior wall, when the trough is positioned in the wearer's mouth.

17. An intraoral discluder as defined in claim 11, wherein the trough is sized and configured to accommodate only the upper or lower incisors.

* * * * *

UNITED STATES PATENT AND TRADEMARK OFFICE
CERTIFICATE OF CORRECTION

PATENT NO. : 7,654,267 B2  Page 1 of 1
APPLICATION NO. : 10/881946
DATED : February 2, 2010
INVENTOR(S) : James P. Boyd It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 840 days.

Signed and Sealed this

Twenty-third Day of November, 2010

David J. Kappos
*Director of the United States Patent and Trademark Office*